(12) United States Patent
Yasunaga et al.

(10) Patent No.: US 8,739,610 B2
(45) Date of Patent: Jun. 3, 2014

(54) SAMPLE INJECTION PORT AND AUTO-SAMPLER HAVING THE SAME

(75) Inventors: Kenichi Yasunaga, Uji (JP); Masami Tomita, Kyoto (JP); Yoshiaki Maeda, Kyoto (JP)

(73) Assignee: Shimadzu Corporation, Kyoto-Shi (JP)

( * ) Notice: Subject to any disclaimer, the term of this patent is extended or adjusted under 35 U.S.C. 154(b) by 249 days.

(21) Appl. No.: 13/124,367

(22) PCT Filed: Oct. 16, 2008

(86) PCT No.: PCT/JP2008/002933
§ 371 (c)(1),
(2), (4) Date: Jun. 28, 2011

(87) PCT Pub. No.: WO2010/044126
PCT Pub. Date: Apr. 22, 2010

(65) Prior Publication Data
US 2011/0247405 A1    Oct. 13, 2011

(51) Int. Cl.
*G01N 30/16*    (2006.01)
(52) U.S. Cl.
USPC ........................................ 73/61.56; 73/864.85
(58) Field of Classification Search
USPC ............................................ 73/61.56, 864.85
See application file for complete search history.

(56) References Cited

U.S. PATENT DOCUMENTS 4,621,534 A * 11/1986 Munari et al. .............. 73/864.86
5,531,810 A * 7/1996 Fullemann .................... 96/105
6,526,812 B2 * 3/2003 Martin et al. ................ 73/61.55
7,105,043 B2    9/2006 O'Neil
2002/0153312 A1 * 10/2002 Gjerde et al. ................ 210/635

FOREIGN PATENT DOCUMENTS

| DE | 20216216 U1 | 2/2003 |
|---|---|---|
| JP | 64-001637 | 1/1989 |
| JP | 04-013653 | 3/1992 |
| JP | 06-148157 | 5/1994 |
| JP | 09-274027 | 10/1997 |
| JP | 2003-098049 | 4/2003 |
| JP | 2003-215118 | 7/2003 |
| JP | 3129670 | 2/2007 |

OTHER PUBLICATIONS

Chinese language office action dated Jul. 3, 2012 and its English language translation issued in corresponding Chinese application 200880131590.4.

(Continued)

*Primary Examiner* — Hezron E Williams
*Assistant Examiner* — Paul West
(74) *Attorney, Agent, or Firm* — Bingham McCutchen LLP

(57) ABSTRACT

A sample injection port 10 for injecting a sample into a chromatograph or other devices is composed of a body 13 made of an inelastic material, a first seal member 14 made of an elastic material and attached to one end of the body part 13, and a second seal member 15 made of an elastic material and attached to the other end of the body part 13. A first through hole formed in the first seal member 14, a second through hole formed in the second seal member 15 and a third through hole formed in the body part 13 are coaxially connected to form an introduction hole for sample injection. With this construction, a sample injection port which has a small inner diameter, is easy to manufacture, and yet capable of achieving a high pressure resistance can be provided.

6 Claims, 4 Drawing Sheets

(56) References Cited

OTHER PUBLICATIONS

Japanese Office Action mailed Jun. 18, 2013 for corresponding Japanese Patent App. No. 2010-533727.

English translation of Reason for Rejection of Japanese Office Action mailed Jun. 18, 2013 for corresponding Japanese Patent App. No. 2010-533727.

* cited by examiner

US 8,739,610 B2

SAMPLE INJECTION PORT AND AUTO-SAMPLER HAVING THE SAME

CROSS-REFERENCE TO THE RELATED APPLICATIONS

This application is a national stage of international application No. PCT/JP2008/002933, filed on Oct. 16, 2008, the entire contents of which are incorporated herein by reference.

TECHNICAL FIELD

The present invention relates to a sample injection port and an auto-sampler (automatic sample injection device) having a sample injection port,

BACKGROUND ART

In an analysis using a liquid chromatograph, an auto-sampler is used to automatically inject a plurality of samples into a column in a predetermined order. A commonly used technique for auto-samplers is the so-called total volume injection method, in which a predetermined amount of sample is collected from a sample bottle and the entirety of the collected sample is injected into a mobile-phase channel. (For example, refer to Patent Document 1.)

In the process of injecting a sample by the total volume injection method, a predetermined amount of sample is initially suctioned from a sample bottle by using a needle. The suctioned sample is charged into a sample loop (measuring loop) connected to the base end of the needle. Subsequently, the needle is inserted into the sample injection port, while the channel configuration of the sample side is changed by means of a channel-switching valve so that the sample loop will be inserted in the mobile-phase channel extending from the mobile-phase container to the column. As a result, the entire amount of the sample charged in the sample loop is pushed forward by the mobile phase, to be injected into the column.

In such an auto-sampler adopting the total volume injection method, it is necessary to minimize the internal volume of the channel to improve the sample-separating performance. Accordingly, in a conventional auto-sampler, the sample injection port is directly attached to the channel-switching valve without using any pipe or similar connecting element. (Refer to Patent Document 2.)

FIG. 8 shows one example of the configuration of the sample injection port and the channel-switching valve in the aforementioned conventional auto-sampler. The channel-switching valve 4 is, for example, a six-port two-position rotary valve, which has six ports, including the sample injection port 100, arranged at regular intervals in a stator 42 provided in the upper part of a casing 41. The sample injection port 100 is plugged vertically in the stator 42, which has internal channels respectively extending from the ports to a rotor 43 fixed to a shaft 44 within the casing 41. The rotor 43 can be rotated in the state of being thrust onto the lower surface of the stator 42 by a spring 45. The rotor 43 has three arc-shaped grooves carved on the sliding surface as paths for connecting the neighboring ports. Rotating the shaft 44 changes the connection state of these ports and thereby alters the channel configuration.

As shown in FIG. 9, the sample injection port 100 has an introduction hole 100a penetrating through the center of its body. The upper mouth of the introduction hole 100a is open at the bottom of a female-tapered needle-seal surface 100b. The sample injection port 100 is made of a polyether ether ketone resin, represented by "PEEK" (registered trademark), or similar material. When a needle 9 is inserted in the sample injection port 100, the tapered tip of the needle 9 fits the female-tapered needle-seal surface 100b, thus establishing between them a liquid-tight connection.

Patent Document 1: JP-A H6-148157
Patent Document 2: JP-A 2003-215118
Patent Document 3: Japanese Registered Utility Model No. 3129670

DISCLOSURE OF THE INVENTION

Problems to be Solved by the Invention

As already stated, in the sample injection device using the total volume injection method, it is necessary to minimize the internal volume of the channel. A technique for addressing this problem is proposed in Patent Document 3, in which the diameter of the introduction hole of the sample injection port is reduced to approximately 0.3 mm so as to decrease the internal volume of the channel in the portion near the sample injection port and thereby prevent the diffusion of the sample to the outside of the column. To further decrease this diffusion, the inner diameter of the introduction hole must be further reduced. However, the introduction hole cannot be shorter than approximately 10 mm since the stator must have a certain thickness so that the aforementioned ports can be attached to it. Boring such a long hole with a diameter less than 0.3 mm by machine is difficult. Another problem exists in that, when a liquid is supplied at a pressure as high as approximately 100 MPa, the needle-seal surface or stator-seal surface of the sample injection port may possibly be deformed since this part is a single-piece element made of PEEK or a similar resin and contains a considerable volume of resin. Such a deformation can cause a leakage of the liquid under certain conditions.

The present invention has been developed in view of these problems, and one objective thereof is to provide a sample injection port which has a small inner diameter, is easy to manufacture, and yet capable of achieving a high pressure resistance, and to provide an auto-sampler having such a sample injection port.

Means for Solving the Problems

A sample injection port according to the present invention aimed at solving the previously described problems is characterized by including:
a) a body made of an inelastic material;
b) a first seal member made of an elastic material and attached to one end of the body; and
c) a second seal member made of an elastic material and attached to another end of the body,
wherein a first through hole formed in the first seal member, a second through hole formed in the second seal member, and a third through hole formed in the body are coaxially connected to form an introduction hole for sample injection.

The sample injection port according to the present invention is composed of a plurality of parts. By attaching the two seal members to both ends of the body, the through holes which are respectively formed in these seal members and the body are serially connected, forming an introduction hole for sample injection. As compared to the conventional sample injection port consisting of a single-piece resin element with an introduction hole machine-bored through the entire length of the port, the construction according to the present invention significantly reduces the length of the through hole to be formed in each part, thus facilitating the formation of the introduction hole. As a result, an introduction hole whose diameter is smaller than in the conventional case can be created. This also means the possibility for reducing the production cost of a sample injection port having an introduction hole whose diameter approximately equals that of the conventional introduction hole. Furthermore, in the sample injection port according to the present invention, the volume of the parts made of a resin or similar elastic material is small, so that the amount of deformation during the liquid-supply operation can be reduced to achieve high pressure resistance.

In the sample injection port according to the present invention, the body may desirably include an introduction tube and a housing for holding the introduction tube, wherein an inner hole of the introduction tube corresponds to the third through hole.

This type of construction eliminates the necessity of boring the third through hole by machine and thereby facilitates the manufacturing of the body. Furthermore, a sample injection port with a small inner volume can be easily created by using a tube with a small inner diameter as the aforementioned introduction tube.

The auto-sampler according to the present invention aimed at solving the previously described problems is an auto-sampler including a needle, a channel-switching valve and a sample injection port provided on the channel-switching valve, the auto-sampler injecting, through the needle, a liquid sample from one end of an introduction hole formed in the sample injection port to introduce the liquid sample into a channel connected to the other end of the introduction hole via the channel-switching valve, wherein the sample injection port is a sample injection port according to the previously described present invention.

Effect of the Invention

As described thus far, the sample injection port according to the present invention is composed of a plurality of separate parts. This type of construction facilitates the formation of the introduction hole and also allows the reduction in the volume of the elastic material to achieve a high pressure resistance.

EXPLANATION OF NUMERALS

10 . . . Sample Injection Port
11 . . . Housing
11a . . . Tube-Insertion Hole
11d . . . Through Hole
12 . . . Tube
13 . . . Body
14 . . . First Seal Member
14a . . . First Through Hole
15 . . . Second Seal Member
15a . . . Second Through Hole
3 . . . Auto-Sampler
4 . . . High-Pressure Valve (Channel-Switching Valve)
41 . . . Casing
42 . . . Stator
43 . . . Rotor

BEST MODE FOR CARRYING OUT THE INVENTION

An auto-sampler and a sample injection port according to one embodiment of the present invention are hereinafter described with reference to the attached drawings.

Figure 1:
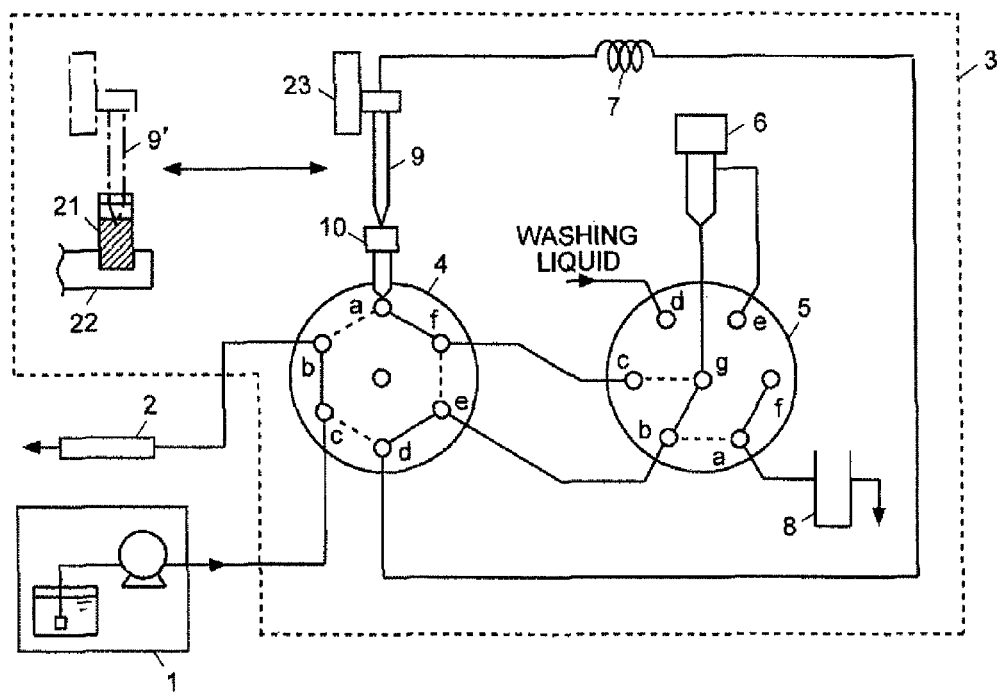
FIG. 1 is a channel configuration diagram of an auto-sampler according to one embodiment of the present invention.

FIG. 1 is a schematic diagram showing one example of the channel configuration of the auto-sampler 3 according to the present embodiment. The auto-sampler 3 in the present embodiment is used for injecting a sample into a column 2 of a liquid chromatograph by a total volume injection method.

In this auto-sampler 3, the high-pressure valve 4 is a six-port two-position rotary switching valve with six ports 4a-4f. The valve position can be changed to selectively connect two ports neighboring each other. More specifically, as shown in FIG. 1, the connection can be switched between the combination of the ports shown by the solid lines and the combination shown by the broken lines. The low-pressure valve 5 is a seven-port six position rotary valve with seven ports 5a-5g. The common port 5g, to which a measuring pump 6 is connected, can be linked to one of the other six ports 5a-5f. In conjunction with this linking operation, two predetermined ports neighboring each other among the six ports 5a-5g are also connected. For example, as shown by the solid lines in FIG. 1, when the common port 5g is linked to the port 5b, the ports 5a and 5f will also be linked. The high-pressure valve 4 in the present embodiment corresponds to the channel-switching valve in the present invention.

A column channel leading to the column 2 is connected to the port 4b of the high-pressure valve 4, while a mobile-phase channel for supplying a mobile phase (solvent) from a liquid supply unit 1 is connected to the port 4c. A needle 9 is connected via a sample loop 7 to the port 4d. The port 4a is the sample injection port 10. The ports 4e and 4f are respectively connected to the ports 5b and 5c of the low-pressure valve 5. The port 5a of the low-pressure valve 5 leads to a washing port 8. The port 5e is connected to the measuring pump 6. A washing liquid is supplied to the port 5d. A small-sized vial 21, with a sample liquid held therein, is contained in a sample rack 22. The needle 9, which can be moved in both horizontal and vertical directions by a moving mechanism 23, can be transferred to a position above the vial 21 or the washing port 8, and then inserted into the liquid held therein.

The basic operational sequence of the present system during the sample-injecting process is hereinafter described. In the sample-collecting phase, the high-pressure valve 4 and the low-pressure valve 5 are switched to the connection state shown by the solid lines in Fig. I. The needle 9 is moved to a position above the vial 21 and then inserted into the sample liquid held therein (as indicated by numeral 9'). In this state, the plunger of the measuring pump 6 is pulled, whereby the sample liquid is suctioned from the vial 21 via the mobile phase (or a washing liquid of the same composition) inside the channel between the measuring pump 6 and the needle 9. The suctioned sample liquid is retained in the sample loop 7. The amount of the collected sample liquid is equal to the suctioning amount of the measuring pump 6.

After the sample is collected, the needle 9 is returned to a position above the sample injection port 10 and then inserted into this port 10. The high-pressure valve 4 is switched to the connection state shown by the broken line in FIG. 1. Then, the mobile phase supplied from the liquid supply unit I flows through the sample loop 7, the needle 9 and the sample injection port 10 into the column 2. In this process, the sample liquid previously held in the sample loop 7 is also sent into the column 2 together with the mobile phase. While passing through this column 2, the sample is separated into components, which are sequentially detected by a detector (not shown).

Figure 2:
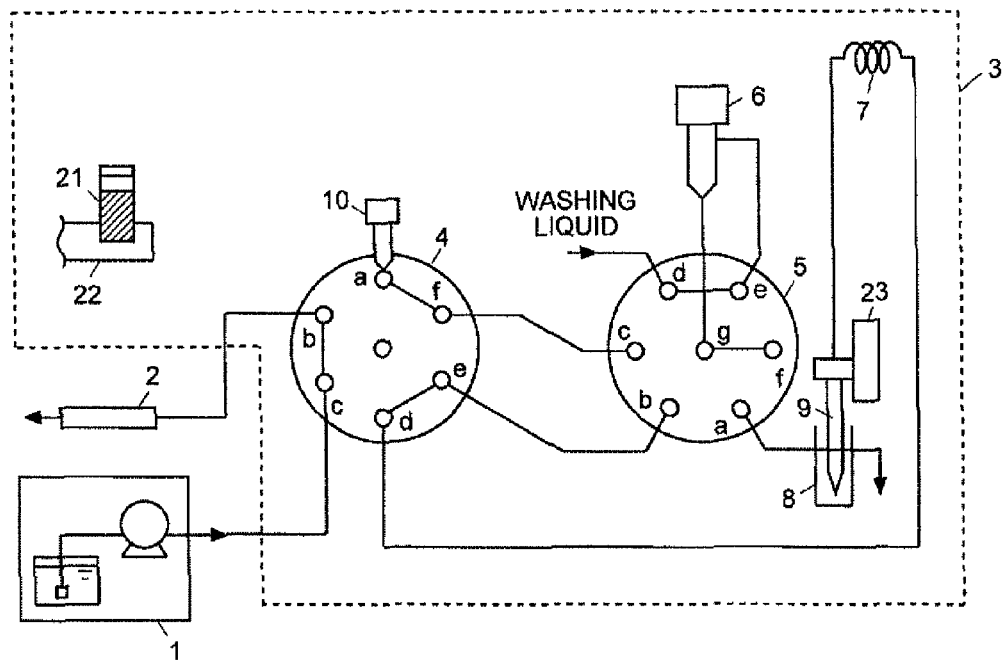
FIG. 2 is a channel configuration diagram for illustrating an operation of the auto-sampler according to the embodiment.

The needle 9, on which the sample liquid attaches when the sample is suctioned, is washed as follows: The high-pressure valve 4 and the low-pressure valve 5 are switched to the connection state as shown by the solid lines in FIG. 2. Then, the plunger of the measuring pump 6 is pulled to suction the washing liquid into the syringe. Subsequently, the high-pressure valve 4 and the low-pressure valve 5 are switched to the connection state as shown by the broken lines in FIG. 1, after which the plunger is pushed to eject the washing liquid from the measuring pump 6. The washing liquid is injected into the washing port 8 and fills the same port. An excessive amount of the washing liquid is discharged from the drain outlet of the washing port 8. Next, as shown in FIG. 2, the needle 9 is moved a position above the washing port 8 and then inserted into the washing liquid held in the washing port 8. After being washed for a specific period of time, the needle 9 is returned to the sample injection port 10.

Figure 3:
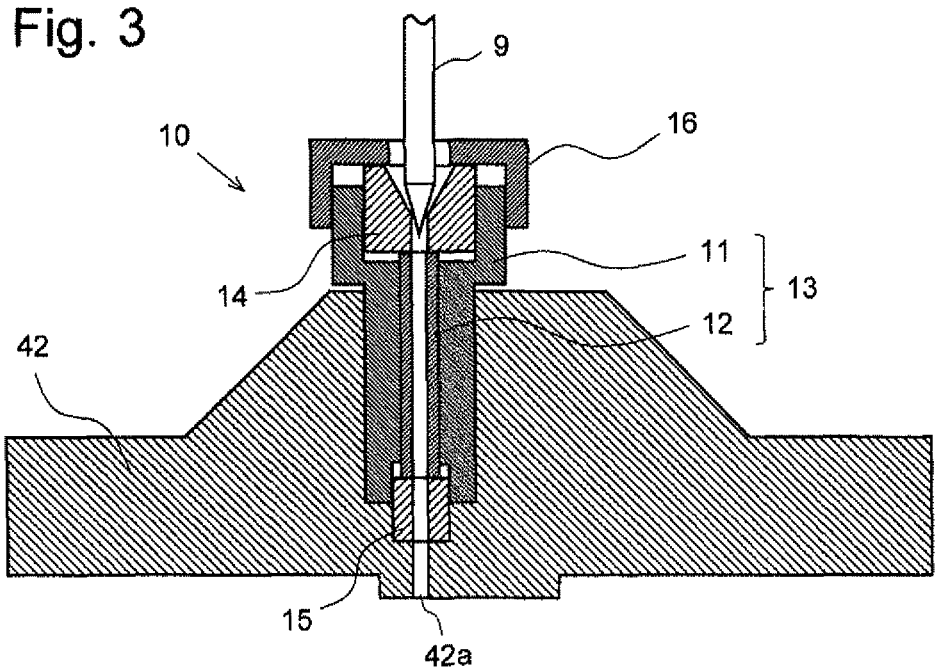
FIG. 3 is a vertical sectional view showing the sample injection port in the auto-sampler of the embodiment.
Figure 4:
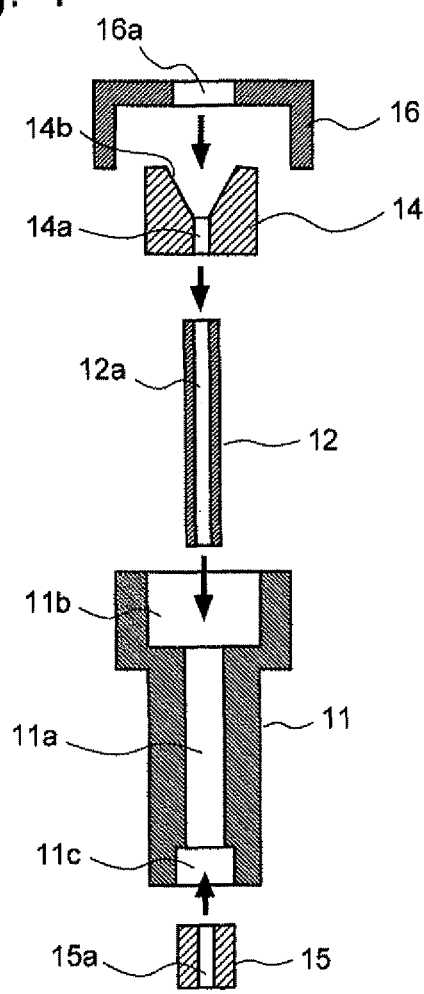
FIG. 4 is an exploded sectional view of the sample injection port in FIG. 3.
Figure 8:
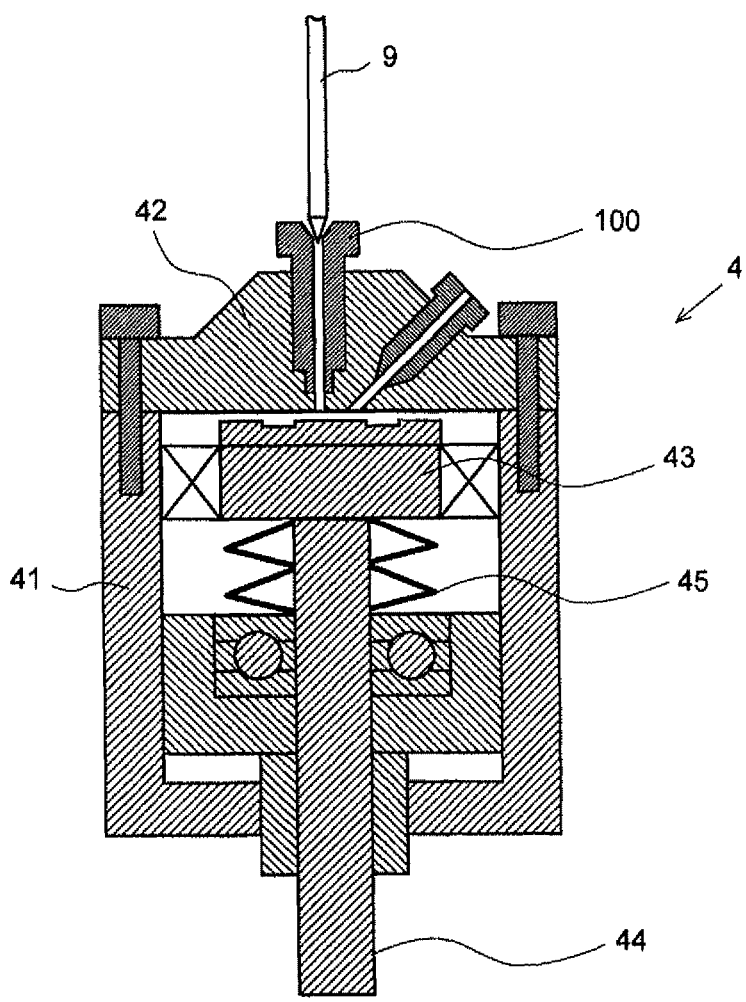
FIG. 8 is a sectional view of one example of the configuration of the sample injection port and the channel-switching valve in a conventional auto-sampler.
Figure 9:
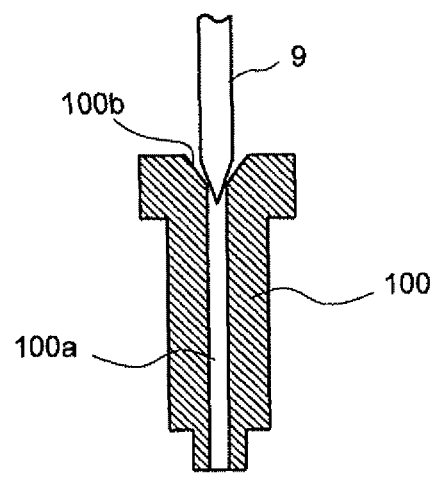
FIG. 9 is an enlarged view of the needle and the sample injection port shown in FIG. 8, with the needle being fitted on the port.

The configuration of the sample injection port 10, which characterizes the auto-sampler 3 according to the present embodiment, is hereinafter described. FIG. 3 is a sectional view showing the structure of the sample injection port 10 used in the auto-sampler 3 of the present embodiment, and FIG. 4 is an exploded sectional view of the sample injection port 10. The structure of the channel-switching valve is the same as shown in FIG. 8 and hence will not be described in detail. In the following description, the vertical direction is defined with reference to the top-to-bottom direction in each figure.

The sample injection port 10 in the present embodiment mainly consists of a body 13, a first seal member 14 and a second seal member 15. The body 13 is composed of a housing 11 and a tube 12, which are both made of stainless steel. The seal members 14 and 15 are both made of the PEEK resin.

Figure 5:
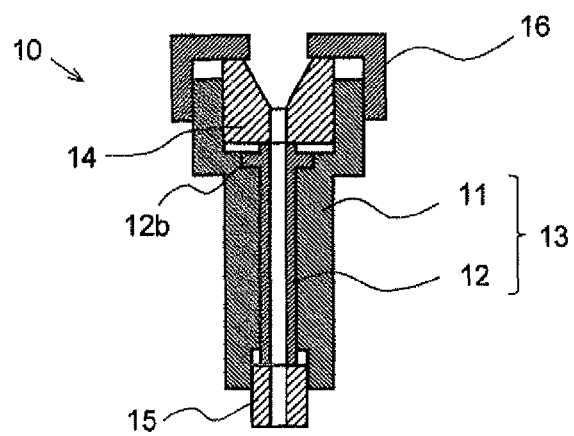
FIG. 5 is a sectional view showing another example of the configuration of the sample injection port in the embodiment.
Figure 6:
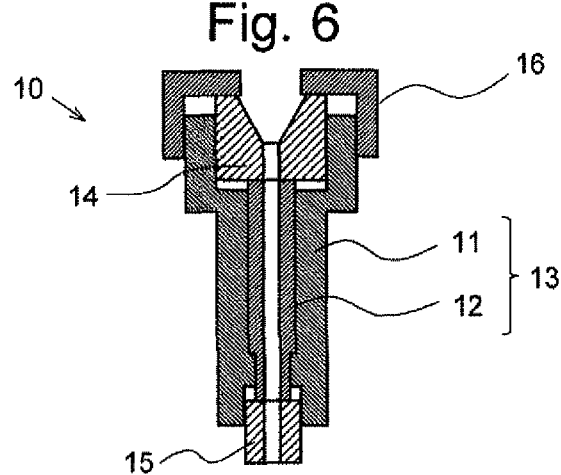
FIG. 6 is a sectional view showing still another example of the configuration of the sample injection port in the embodiment.

Inside the housing 11, a vertically penetrating tube-insertion hole 11a is formed, in which the tube 12 is fixed. For example, this tube can be fixed by pressing it into the tube-insertion hole I la or welding it to the housing 11. Alternatively, as shown in FIG. 5, the tube 12 may be provided with a flange-like projection 12b extending in the radial direction from the upper portion of the circumferential surface thereof, in which case the tube 12 can be fixed in the tube-insertion hole I la by engaging the projection 12b with the circumferential edge of the upper mouth of the tube-insertion hole 11a. Another example is shown in FIG. 6, in which a step portion is formed at both the inner circumference of the tube-insertion hole 11 a and the outer circumference of the tube 12 so that the tube 12 can be fixed in the tube-insertion hole 11a by engaging the two step portions with each other. In the example of FIG. 6, the outer diameter of the lower portion of the tube 12 is smaller than that of the upper portion thereof, and the inner diameter of the lower portion of the tube-insertion hole 11a is appropriately chosen so as to allow the passage of the lower portion of the tube 12 while preventing the passage of the upper portion thereof. Accordingly, when the tube 12 is inserted from the upper mouth of the tube-insertion hole 11a, the tube 12 is fixed at a predetermined position inside the tube-insertion hole 11a.

As shown in FIGS. 3-6, it is preferable to make the upper and/or lower end of the tube 12 slightly project from the mouth of the tube-insertion hole 11a so that the tube 12 comes in contact with the lower surface of the first seal member 14 or the upper surface of the second seal member 15 only at the end face of the tube 12. According to this design, the area of the seal surface can be made smaller to achieve a higher pressure resistance. The tube 12 should preferably have its inner surface mirror-polished. This makes the sample components passing through the tube 12 less likely to remain on the inner wall of this tube 12, whereby the carryover of the sample components is reduced.

Furthermore, a first hollow portion 11b for receiving the first seal member 14 is formed in the upper portion of the housing 11. Similarly, a second hollow portion 11c for receiving the second seal member 15 is formed in the lower portion of the housing 11. The first seal member 14 received in the first hollow portion 11b can be fixed by screwing a stainless cap 16 onto the upper part of the housing 11. The cap 16 has an opening 16a for allowing the passage of the needle 9.

The first and second seal members 14 and 15 are provided with the first and second through holes 14a and 15a vertically penetrating through the respective seal members. A female-tapered needle-seal surface 14b is formed on the upper side of the first seal member 14, with the upper mouth of the first through hole 14a being open at the bottom of the needle-seal surface 14b.

When the seal members 14 and 15 are respectively fitted into the hollow portions 11b and 11c at the upper and lower ends of the housing 11, the first through hole 14a, the inner hole 12a of the tube 12, and the second through hole 15a are coaxially connected. As a result, an introduction hole continuously extending from the mouth on the upper surface of the first seal member 14 to the mouth on the lower surface of the second seal member 15 is formed. That is to say, the tube 12 in the present embodiment corresponds to the introduction tube in the present invention, while the first through hole 14a, the second through hole 15a and the inner hole 12a of the tube 12 respectively correspond to the first through hole, the second through hole and the third through hole in the present invention.

When the sample injection port 10 is attached to the stator 42 of the high-pressure valve 4, the second seal member 15 exhibits a sufficient sealing performance for the stator 42, whereby the channel 42a formed in the stator 42 and the introduction hole of the sample injection port 10 are connected in a liquid-tight manner. When a liquid sample is injected through the needle 9 into the sample injection port 10, the first seal member 14 exhibits a sufficient sealing performance for the needle 9, so that the sample can be injected with no leakage of the liquid.

As described thus far, unlike the conventional sample injection port which is molded as a single-piece part made of resin, the sample injection port according to the present embodiment is composed of a plurality of separate parts. These parts can be easily manufactured since there is no need to bore a deep hole with a small diameter through each part.

Accordingly, a sample injection port whose performance is comparable to that of the conventional product can be manufactured at lower costs. Furthermore, it is also possible to create a sample injection port having a smaller inner diameter and higher performance (e.g. with less diffusion of the sample) than those of the conventional product. As compared to the conventional single-piece sample injection port which is entirely made of resin, the parts of the present device require a smaller volume of elastic material and hence undergo only a minor deformation, so that a high pressure resistance can be achieved.

Figure 7:
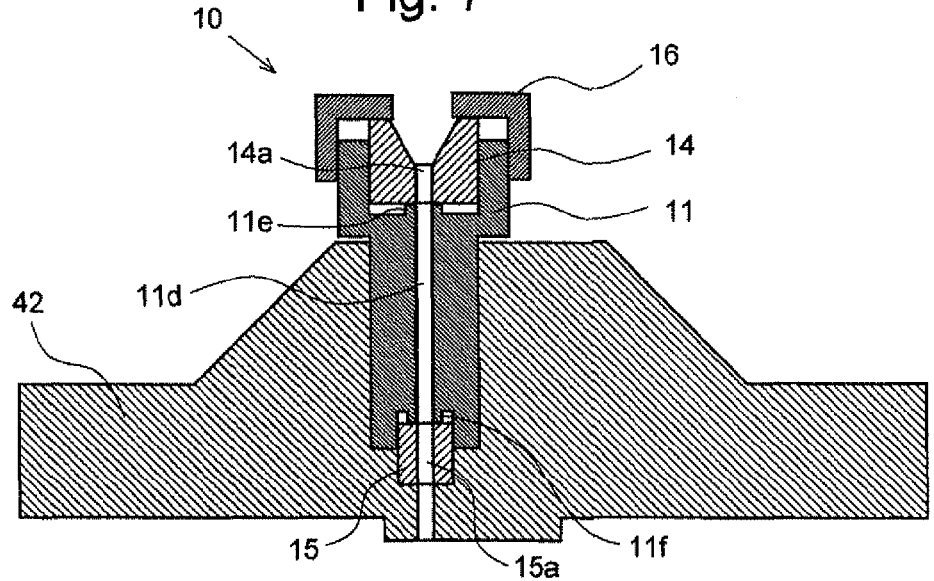
FIG. 7 is a sectional view showing still another example of the configuration of the sample injection port in the embodiment.

As described previously, the sample injection port used in the auto-sampler 3 of the present embodiment includes the tube 12 inserted into the housing 11. FIG. 7 shows another example of the structure of the sample injection port, in which a through hole lid for the passage of the sample is directly formed through the housing 11, When the first and second seal members 14 and 15 are respectively put into the hollow portions 11b and 11c provided in the upper and lower ends of the housing 11, the through holes 14a and 15a respectively formed in the seal members 14 and 15 as well as the through hole I ld formed in the housing 11 are coaxially connected to function as an introduction hole for sample injection. In the present example, the through hole 11d corresponds to the third through hole in the present invention. The through hole 11d of the housing 11 in the present example should preferably also have the circumference edge of its upper and/or lower mouth projected in the axial direction so that the projections lie and 11f will respectively come in contact with the seal members 14 and 15 at a small sealing area.

The present invention has been thus far described by means of an embodiment. It should be noted that the present invention is not limited to the previous embodiment but can be appropriately changed within the spirit of the present invention. For example, although the sample injection port according to the present invention is particularly effective in an auto-sampler using a total volume injection method, it may also be used in an auto-sampler using a partial volume injection method. The auto-sampler according to the present invention is available not only for a liquid chromatograph; it may also be used for injecting a sample in any other type of analyzing device.

Furthermore, the housing and the tube, which were made of stainless steel the previous embodiment, may be made of any kind of inelastic material with corrosion resistance, For example, titan may be used to create them. Similarly, the first and second seal members, which were made of the PEEK resin in the previous embodiment, may be made of any kind of elastic material with corrosion resistance. For example, a type of resin marketed as "Vespel" (registered trademark) may be used to create those members.

The introduction holes formed in the sample injection port shown in FIGS. 3-7 have the same diameter from the mouth in the upper surface of the first seal member to the mouth in the lower surface of the second seal member. It is also possible to change the diameter of the through hole for each part, or to vary the inner diameter of the through hole within a single part. Based on this idea, for example, the introduction hole may be designed so that it has a sufficient inner diameter in its upper portion to allow the insertion of the tip of the needle and a smaller inner diameter in its lower portion to reduce its inner volume.

The invention claimed is:

1. A sample injection port comprising:
   a) a body made of an inelastic material;
   b) a first seal member made of an elastic material and attached to one end of the body, the first seal member having a female-tapered needle-seal surface formed on a side to fit the tip of a needle; and
   c) a second seal member made of an elastic material and attached to another end of the body, wherein: a first through hole formed in the first seal member, a second through hole formed in the second seal member, and a third through hole formed in the body are coaxially connected to form an introduction hole for passing a sample injected into the first through hole by the needle; and a circumferential edge of at least one of two mouths of the third through hole is projected in an axial direction of the third through hole so that an end of the projection comes in contact with the first seal member or the second seal member.

2. The sample injection port according to claim 1, wherein the body comprises an introduction tube and a housing for holding the introduction tube, and an inner hole of the introduction tube corresponds to the third through hole.

3. An auto-sampler including a needle, a channel-switching valve and a sample injection port provided on the channel-switching valve, the auto-sampler injecting, through the needle, a liquid sample from one end of an introduction hole formed in the sample injection port to introduce the liquid sample into a channel connected to the other end of the introduction hole via the channel-switching valve, the sample injection port comprising:
   a) a body made of an inelastic material;
   b) a first seal member made of an elastic material and attached to one end of the body, the first seal member having a female-tapered needle-seal surface formed on a side to fit the tip of the needle; and
   c) a second seal member made of an elastic material and attached to another end of the body, wherein: a first through hole formed in the first seal member, a second through hole formed in the second seal member, and a third through hole formed in the body are coaxially connected to form an introduction hole for passing a sample injected into the first through hole by the needle; and a circumferential edge of at least one of two mouths of the third through hole is projected in an axial direction of the third through hole so that an end of the projection comes in contact with the first seal member or the second seal member.

4. The auto-sampler according to claim 3, the body of the sample injection port comprises an introduction tube and a housing for holding the introduction tube, and an inner hole of the introduction tube corresponds to the third through hole.

5. A sample injection port comprising:
   a body made of an inelastic material;
   a first seal member made of an elastic material and attached to one end of the body, the first seal member configured to have a female-tapered needle-seal surface formed on a side for fitting the tip of a needle to form a seal; and
   a second seal member made of an elastic material and attached to another end of the body,
   wherein a first through hole formed in the first seal member, a second through hole formed in the second seal member, and a third through hole formed in the body are coaxially connected to form an introduction hole for passing a sample injected into the first through hole by the needle; and a circumferential edge of at least one of two mouths of the third through hole is projected in an axial direction of the third through hole so that an end of the projection comes in contact with the first seal member or the second seal member.

6. The auto-sampler according to claim 5, the body of the sample injection port comprises an introduction tube and a housing for holding the introduction tube, and an inner hole of the introduction tube corresponds to the third through hole.

* * * * *